United States Patent

Goldblum

[11] Patent Number: 6,001,113
[45] Date of Patent: *Dec. 14, 1999

[54] DISPOSABLE CURETTE AND METHOD OF MANUFACTURING THE SAME

[76] Inventor: Orin M. Goldblum, 194 Mayfair Dr., Pittsburgh, Pa. 15228

[ * ] Notice: This patent issued on a continued prosecution application filed under 37 CFR 1.53(d), and is subject to the twenty year patent term provisions of 35 U.S.C. 154(a)(2).

[21] Appl. No.: 08/730,740

[22] Filed: Oct. 15, 1996

Related U.S. Application Data

[63] Continuation of application No. 08/323,858, Oct. 17, 1994, abandoned.

[51] Int. Cl.⁶ ................................................. A61B 17/22
[52] U.S. Cl. .......................... 606/160; 606/167; 606/131
[58] Field of Search ................ 606/1, 107, 131, 606/167–171, 160, 161, 179, 180, 184, 185; 30/301

[56] References Cited

U.S. PATENT DOCUMENTS

| | | | |
|---|---|---|---|
| 809,119 | 1/1906 | Leuchs | 606/160 |
| 1,002,377 | 9/1911 | Ekenborg | 606/160 |
| 1,089,019 | 3/1914 | Swasey . | |
| 2,569,237 | 9/1951 | Hall | 128/304 |
| 2,617,420 | 11/1952 | Jozefczyk | 128/304 |
| 2,651,068 | 9/1953 | Seko | 15/111 |
| 3,502,082 | 3/1970 | Chatfield | 128/304 |
| 4,044,770 | 8/1977 | Ocel et al. | 128/304 |
| 4,414,974 | 11/1983 | Dotson et al. | 128/305 |
| 4,705,035 | 11/1987 | Givens | 606/166 |
| 4,785,796 | 11/1988 | Mattson | 128/9 |
| 4,791,924 | 12/1988 | Kelman | 128/303 |
| 4,932,957 | 6/1990 | Zwick | 606/160 |
| 5,116,346 | 5/1992 | Yeh | 606/160 |
| 5,269,787 | 12/1993 | Cozean et al. | 606/171 |

FOREIGN PATENT DOCUMENTS 1192654   2/1968   United Kingdom .

OTHER PUBLICATIONS

A Disposable Curette For Periosteal Removal Journal Of Dermotologic Surgery & Oncology 20:402–3, 1994.

Primary Examiner—Glenn K. Dawson
Attorney, Agent, or Firm—Webb Ziesenheim Logsdon Orkin Hanson, P.C.

[57] ABSTRACT

A disposable, loop-form surgical curette blade formed as an integral unit from a single elongated blank so as to have the loop-form cutter formed by one sharpened end portion of the blank and a shank formed by the balance of the blank and extending from the loop-form cutter. A method of manufacturing such a blade is also disclosed.

12 Claims, 1 Drawing Sheet

DISPOSABLE CURETTE AND METHOD OF MANUFACTURING THE SAME

This is a continuation of application Ser. No. 08/323,858 filed on Oct. 17, 1994, "now abandoned."

BACKGROUND OF THE INVENTION

This invention relates to curettes of the type used for such purposes as removal of cancerous and non-cancerous skin growths.

The technique of curettage is routinely used by dermatologists to separate diseased skin or skin lesions from normal skin. The instrument used to perform curettage on the skin is termed a dermal curette. Commonly used dermal curettes include, among others, the Fox curette and the Piffard curette, both of which are manual stainless steel instruments having a loop-form cutter or blade and an elongated handle for manipulation of the blade by the user. These are regarded as permanent, reusable curettes, in that because of their expense, they would not be economical for single-use application.

Disposable curettes are also available and are generally suitable for their intended purpose. However, they often may have a different feel to the user, and therefore may require practice before the user who is accustomed to a reusable curette, such as the Fox or the Piffard, can become proficient in their use. The reason for this is that normal tissue has a different feel under the cutting action of the curette than lesional tissue. The user who is more sensitive to this difference in feel will also be more proficient at removal of lesions, since the sensitivity to feel will allow more complete removal of lesional tissue with less incursion into normal tissue.

This sort of sensitivity comes with practice and experience, and can be disrupted by differences in design, materials and structure, as between different curettes. Accordingly, practitioners would normally prefer to confine their use of curettes to a single type. The need to choose a single type of curette could, however be obviated by a disposable curette having the same feel, heft, weight and balance as a reusable curette.

Of course, the disposability of a curette is entirely a matter of economics, and any curette may be regarded as disposable if the user is unconcerned about its cost. As a practical matter, however, many physicians, including dermatologists for example, use curettes routinely and therefore cannot treat reusable curettes as disposables, nor can they escape the cost trade-off between presently available reusable and disposable curettes.

The cost of a reusable curette is relatively high compared to available disposable curettes, and the instrument therefore must serve the user over a relatively long term in order to justify its cost. Typically, after a period of use, the cutting blade of a reusable curette will become dull and must be sent out for resharpening. In addition, there are the costs of time, material, equipment, energy and labor involved in the repeated cleaning and sterilization of reusable curettes. Still further, a practitioner who sees patients in more than one examination room, or in multiple office locations, will require duplicate sets of such instruments to ensure that a set of suitable, freshly sterilized, sharp curettes are always available in each examination room or office location while others are being sterilized or sharpened. As may be appreciated, the costs associated with curette procurement and maintenance can be substantial.

Of course, many of the logistical and financial drawbacks attendant to the use of reusable curettes disappear entirely if one instead chooses to use only disposable curettes. However, disposable curettes also have their associated drawbacks.

Specifically, presently available disposable curettes are comprised of an inseparable handle and stainless steel blade assembly which is intended to be disposed of entirely after a single use. Thus, although sharpening, cleaning or sterilization costs do not arise, the full replacement cost of the curette, while much lower than the cost of a reusable curette, must be paid with each use.

Another disadvantage of some disposable curettes is the use of a rather thin gauge material for the loop-form cutting blade. A curette blade formed of such thin gauge material may tend to deform under mechanical pressure and therefore will not have a consistent feel in use. Thus, an unduly thin gauge curette blade may be more difficult to control and use, regardless of the experience of the user.

Additionally, presently available disposable curettes may tend to be less sharp than either a new or resharpened reusable curette. This may be due to mechanical limitations encountered in the sharpening of the thin gauge blade material.

A final disadvantage of presently available disposable curettes is the lightweight plastic handle which does not have the same feel or shape as the stainless steel handle of a reusable curette. No choice of handle is available since these disposable curettes are all manufactured with the same handle style.

Among the prior art relating to curettes in general are U.S. Pat. Nos. 2,569,237, 2,617,420, 2,651,068, 4,044,770, 4,785,796, 4,791,924, 4,932,957 and 5,116,346, as well as British Patent 1,192,654. Several of these patents disclose curette instruments with a loop-form blade or a non-cutting loop-form working end. Other examples of related art include U.S. Pat. Nos. 1,089,018, 3,502,082 and 4,414,974.

BRIEF SUMMARY OF THE INVENTION

The present invention contemplates a disposable curette in the form of a sturdy and sharp curette blade having a loop-form cutter portion and an elongated shank portion by which the disposable blade may be attached to a conventional scalpel blade handle. In order to make this disposable blade of suitable strength and sharpness, and therefore of comparable feel to a conventional reusable curette, the material from which it is formed is to be of a sufficient gauge or thickness, as will be described. To offset the additional cost of better material, a specific blade structure is utilized which minimizes the material for each blade, thereby achieving a cost generally in line with that of disposable curettes, which may be neither as sturdy nor as sharp.

An additional factor in this favorable cost comparison is that only the blade is disposed of after use, the handle being a conventional handle of the operator's preference, such as commonly used heretofore to hold a disposable scalpel blade. More specifically, the disposable curette blade of the present invention contemplates an elongated blank stamped from surgical grade stainless steel and formed with an elongated blade or cutter portion extending adjacent one end of the blank and an elongated shank portion extending adjacent the opposed end of the blank. The blade portion is formed into a loop to provide the loop-form cutting blade, and the shank portion extends therefrom to be received by the blade attachment portion of a conventional scalpel blade handle.

In several alternative embodiments of the invention, different structures for the loop-form cutting blade are contemplated, but all are intended to provide a curette blade which offers the sharpness, heft or mass, and rigidity, and hence the overall feel of a conventional reusable curette, without nearly the cost of procurement or the cost and inconvenience of cleaning, sterilizing and resharpening.

Accordingly, it is one object of the present invention to provide a novel and improved disposable curette blade, such as a dermal curette, and a novel and improved method of manufacturing such a curette blade.

A further object of the invention is to provide an improved loop-form curette blade formed from an elongated blank having one end portion thereof which forms the loop-form blade and the opposed end portion thereof forming a shank which extends from the loop-form blade.

These other objects and further advantages of the invention will become more readily apparent upon consideration of the following detailed description and the accompanying drawings, in which.

All disclosure herein relating to the structure and fabrication of my novel curette blade is to be understood as disclosure of both my novel method and structure, even though such disclosure may not be otherwise characterized as method.

Figure 1:
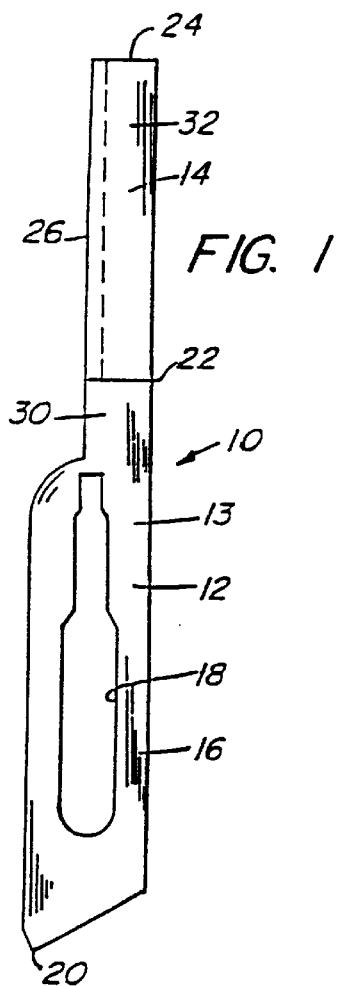
FIG. 1 is a side elevation of a blank from which a disposable curette blade according to the present invention is formed.

There is generally indicated at 10 in FIG. 1 a disposable curette blade according to one presently preferred embodiment of the instant invention, and comprising a single piece or unitary blade structure 12 which is stamped as a blank from a suitable material.

Although blade 12 may be fabricated from either surgical grade carbon or stainless steel, the preferred material is surgical grade stainless steel of the 300 or 400 series. Specifically, the American Society for Testing and Materials has listed stainless steel types for curettes to include types 302, 303, 410, 416 and 420. Of course, other materials and material types may be equally suitable for the described blade.

Blade 12, as noted, is comprised of a single elongated cutter portion 14 extending from one end 24 thereof and an elongated shank portion 16 extending from the opposed end 20 thereof.

As noted, shank 16 may be formed to cooperate with any known scalpel blade handle, such as a Bard-Parker or Bard-Parker-style handle, or a Beaver or Beaver-style chuck handle. Of course, the shank 16 may be formed for retention by other types of suitable blade handles as well.

The blade shank 16 as shown includes a notched aperture 18 by which the blade is cooperable with a Bard-Parker or Bard-Parker-style handle, for example one which accepts a #15 scalpel blade. As is well known, the Bard-Parker or Bard-Parker-style handle includes a blade attachment portion which would correspond to the aperture 18 in order to receive the shank 16 in a reversible locking engagement whereby the blade 10 is retained and secured in place with respect to the Bard-Parker or Bard-Parker-style blade handle.

In one alternative configuration for shank 16, not shown herein, the shank 16 may be formed without a notched aperture, such shank conforming to the slotted blade opening of a Beaver or Beaver-style chuck collet. When the chuck collet is attached to the Beaver or Beaver-style handle by threaded engagement therewith and screwed on to the handle, the resulting clamping action securely retains the blade shank 16. This self-locking collet mechanism is well known.

In another alternative configuration for shank 16, not shown herein, the shank 16 may be formed without a notched aperture, but to include a small circular opening in the middle of the shank near end 20, which conforms with a corresponding projection on the slotted blade opening of a Beaver lok-Collet chuck. When the Lok-Collet chuck is attached to the Beaver handle by threaded engagement therewith and screwed on to the handle, the resulting clamping action securely retains the blade shank 16. This self-locking collet mechanism is also well known.

Further description of the handle structures discussed hereinabove, or other conventional handle structures for use with blade 10, is believed to be unnecessary for an understanding of the present invention. Suffice it to note in this regard that whatever the handle structure contemplated, the shank 16 which is formed to cooperate with such a handle is comprised of a single elongated portion of the curette blade body 13 extending from one longitudinal end, for example longitudinal end 20 of the body 13.

The ideal thickness of the material from which the disposable curette blade can be made is directly dependent upon the style of handle used to cooperate with the blade. An ideal material, and hence blade thickness of 0.015 inches is compatible with the Bard-Parker and Bard-Parker-style handles. An ideal material, and hence blade thickness of 0.025 inches is compatible with the Beaver and Beaver-style chuck handles. Suffice it to say, the thickness of the material from which the disposable curette can be made is dependent upon structural features inherent in the cooperable handle.

Cutter portion 14 is an elongated portion extending from a juncture 22 with shank portion 16 to the opposed end 24 of blade body member 13. The cutter portion 14 is preferably of uniform width and thickness and includes a sharpened edge 26 extending essentially throughout the length thereof. The sharpened edge can be provided by performing suitable grinding on thereof either prior to formation of the cutter portion 14 into its final loop-like form, or after cutter portion 14 is formed into its final bodily shape.

Figure 2:
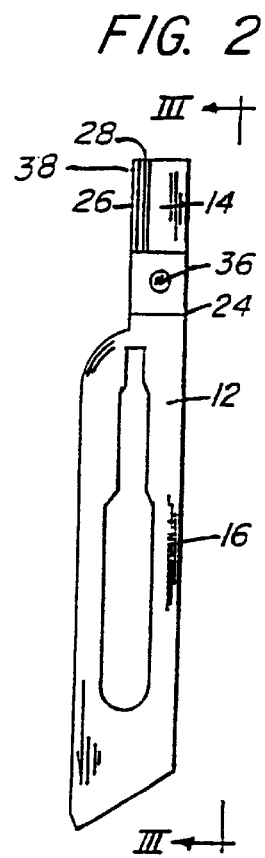
FIG. 2 is a side elevation similar to FIG. 1 showing the upper end portion of the blank formed as a loop-form cutter or blade.
Figure 3:
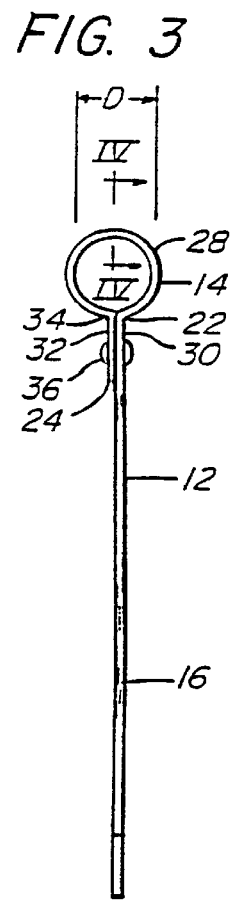
FIG. 3 is a rear elevation taken on line III—III of FIG. 2.

Referring more specifically to FIGS. 2 and 3, the cutter portion 14 is formed by bending thereof into a loop-form cutter 28, which may be either circular or elliptical, for example. In addition, the loop-form or shape of cutter portion 14, which is achieved by bending the cutter portion 14 back upon itself, may produce a shape which is either generally cylindrical or generally conical, although, of course, it will be appreciated that to produce a conical shape, the cutter portion 14 (as shown in FIG. 1) would have to extend along an arc rather than as a straight extension. Alternatively, a conical shape can be produced by bending the cutter portion 14 back upon itself in such a manner that the upper and lower portions of cutter portion 14 are bent into unequal circular or elliptical loops.

As noted, the loop-form cutter 28 is formed by bending cutter portion 14 around itself so that free end 24 resides adjacent a portion 30 of shank 16 next to juncture 22. Accordingly, curette blade 12 is comprised of a single unitary length of blade material having a shank 16 formed from a single elongated extent of the blade body extending from one end thereof, and a loop-form cutter portion formed by a single elongated portion of the blade body extending from the opposed end thereof. This structural feature is common to all disclosed embodiments of the invention.

As shown in FIGS. 2 and 3, one embodiment of the invention contemplates forming the loop-form cutter portion 28 by producing an arcuate bend beginning generally in the vicinity of juncture 22, the bend being of suitable radius to produce a loop of proper dimensions for use as a blade, for example with a cutter diameter ranging from 2 to 8 millimeters. The cutter diameter size may be stamped on the shank of the disposable curette blade to designate the size of the loop-form cutter.

A terminal end portion 32 of cutter portion 14 adjacent longitudinal end 24 is maintained in a straight configuration and a suitable bend 34 forms a juncture between portion 32 and the arcuate curvature of loop-form cutter 28, to thereby allow end portion 32 to reside adjacent the portion 30 of shank 16. A suitable attachment means such as a stainless steel rivet 36 is affixed in mutually registered openings (not shown) through the portions 30 and 32 to fixedly secure these portions together and thereby retain the loop-form shape of cutter portion 28. Alternatively, for this and other described embodiments where a fastener such as the rivet 36 is described, the rivet may be substituted by a spot weld or other suitable fastening means.

As noted hereinabove, the sharpened edge 26 may be provided by grinding blade portion 14 either prior to or after forming thereof into the loop-form cutter 28. If the sharpened edge 26 is provided prior to forming blade portion 14 into the loop-form cutter, the preferred material for fabrication is an austenitic stainless steel, for example type 302 or 303. These non-heat treatable stainless steels are preferred because if a heat treatable material were used, the heat treating would preferably be done before the grinding operations, and therefore also before forming. This would substantially limit the formability of the material and the material would fracture during the forming process.

If the sharpened edge 26 is provided after forming blade portion 14 into the loop-form cutter, the preferred material for fabrication is a martensitic stainless steel, for example type 410, 416 or 420. These heat treatable stainless steels are preferred since heat treating after forming will result in a stronger blade structure.

Figure 4:
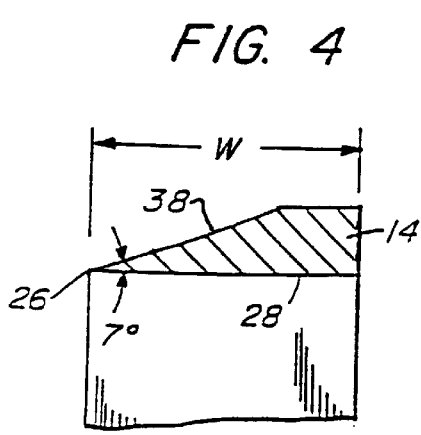
FIG. 4 is an enlarged fragmentary portion of the loop-form cutter of FIG. 2.

In a preferred method, the sharpened edge 26 is provided before loop-form cutter 28 is formed as above described. As shown in FIG. 4, the sharpened edge 26 may be produced by grinding an angle of 7 degrees on the outside aspect of blade portion 14 as indicated at 38.

Of course, it will be appreciated that the scale of FIG. 4 has been greatly enlarged, even more so than the enlarged scale of FIGS. 1 to 3, in order to clearly show the detail of sharpened edge 26. An appreciation for the actual size of the structure shown in FIG. 4 is gained by noting that the overall width W of portion 28 may be approximately 0.125 inches, for example.

In this preferred form of providing a sharpened edge 26 before loop-form cutter 28 is formed, the ground edge may also be placed alternatively on the inside aspect of blade portion 14 or on both the outside and inside aspects of blade portion 14. Placing the ground edge on the outside aspect of blade portion 14 is preferred because this results in a somewhat conical shaped loop-form cutter, a shape that resembles the blade portion of a reusable curette.

As noted above, the sharpened edge 26 may alternatively be provided by performing suitable sharpening operations on blade portion 14 after forming thereof into the loop-form cutter 28. The sharpened edge can be provided by grinding an angle of 7 degrees on the outside aspect of the loop-form cutter. This method is less preferred because grinding the inside, the outside or both the inside and outside aspects of loop-form cutter 28 is a difficult operation.

If sharpened edge 26 of blade portion 14 is provided after forming thereof into the loop-form cutter 28, the entire blade structure is preferably heat treated prior to grinding, according to American Society for Testing of Materials published standards for the heat treating of stainless steels for surgical instruments.

Figure 5:
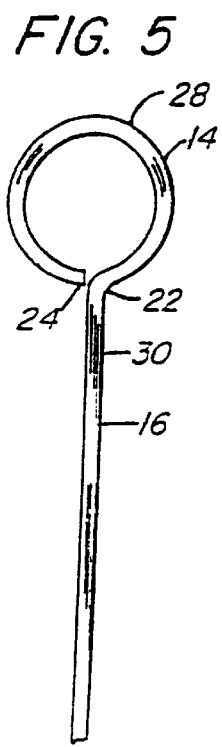
FIG. 5 is an enlarged, fragmentary rear view similar to FIG. 3 showing an alternative embodiment of the invention.
Figure 6:
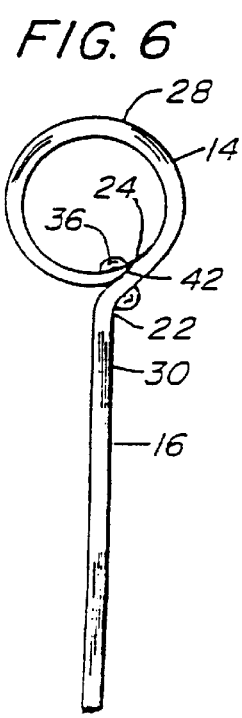
FIG. 6 is an enlarged, fragmentary rear view similar to FIG. 3 showing another alternative embodiment of the invention.

FIGS. 5 and 6 show alternative embodiments of the invention which are essentially similar to the embodiment above described, but with differences as follows. In FIG. 5, the blade shank 16 includes the portion 30 and a bend generally coinciding with juncture 22 where the arcuate form of cutter 28 begins. Again, the bend radius of cutter portion 28 is suitable to form cutter 28 as an essentially closed loop. For the FIG. 5 embodiment however, longitudinal end 24 of cutter portion 14 turns back upon portion 30 and resides adjacent to juncture 22 where the initial bend occurs between shank 16 and cutter portion 14. The longitudinal end 24 may abut shank 16 adjacent juncture 22, or as shown, may be spaced slightly therefrom. With either variation, the loop-form cutter is produced as an essentially complete loop.

FIG. 6 illustrates yet another embodiment of the invention in which shank 16 again includes a portion 30 adjacent the juncture 22 where an initial bend is formed between shank 16 and cutter portion 14. Cutter portion 14 is formed, as in other described embodiments, by bending thereof into an arcuate form to provide the loop-form cutter 28. However, in the FIG. 6 embodiment, the longitudinal end 24 extends back upon that part of cutter portion 14 adjacent to juncture 22 and is formed to nest within the initial arcuate curvature 42 of loop-form cutter 28. The cutter end 24 may be retained with respect to the adjacent part of cutter portion 14 as by a suitable stainless steel rivet 36 passed through suitable, mutually registered apertures (not shown), or alternatively by spot welding.

A sharpened edge for the embodiments of FIGS. 5 and 6 may be provided in essentially the same manner as described above for other embodiments. Grinding may be performed either prior to or after formation of the loop-form cutter 28, but this operation is preferably performed prior to formation of the loop-form cutter for the same reason as described for previous embodiments.

A preferred method of manufacturing the curette blade structure, as described with reference to any embodiment is as follows: first, stamp the single elongated blank; second, surface grind a sharp cutting edge on blade portion 14; third, press form the loop-form cutter 28; and last, retain the loop-form cutter shape by fastening free end 24 to portion 30 of shank 16. As will be appreciated from the above description, the manufacturing method may also include suitable heat treating as specified, and may exclude the fastening of free end 24 as in the FIG. 5 embodiment.

According to the description hereinabove, the present invention contemplates a novel and improved disposable, single use curette blade offering the benefits of minimal cost achieved through minimal material requirements and simplified mechanical fabrication, but having the feel of a reusable curette.

Of course, I have envisioned certain modified and alternative embodiments of the invention, and surely such would also occur to others versed in this alt once they were apprised of my invention. For example, although the loop-form cutter is shown as being symmetrical about the plane of the blade body, it may alternatively be formed asymmetrically with respect to the plane of the blade body. Further, as noted above, the loop-form cutter may be of alternative forms such as elliptical or conical, or a combination of these geometries. Still further, the sharpened edge may extend through all or only a part of the 360 degree extent of the loop-form cutter, and may be either symmetrically or asymmetrically positioned with respect to the plane of the blade body, although preferably the sharpened edge will extend substantially throughout the 360 degree extent of the loop-form cutter, and in a symmetrical structure as above described, substantially throughout the 180 degree extent of the loop-form cutter on either side of the plane of the blade body. Accordingly, it is my intention that the invention should be construed broadly and limited only by the scope of the claims appended hereto.

I claim:

1. A disposable, single use curette blade comprising:

an elongated, unitary body member having an integrally formed shank portion, juncture portion and cutter portion with said juncture portion being disposed intermediate said shank portion and said cutter portion to connect said shank portion to said cutter portion;

said shank portion extending longitudinally from said juncture portion in one longitudinal direction and in the shape of a single band of material of a substantially uniform thickness, wherein only said shank portion of said curette blade extends in said one longitudinal direction beyond said juncture portion, said shank portion including means for cooperation with a handle to selectively, releasably retain said curette blade with respect to such a handle;

said cutter portion having at least one edge which forms a sharp cutting edge;

said cutter portion comprising a portion of said body member extending from said juncture portion as a generally arcuate means having a pair of end portions disposed adjacent said juncture portion and said at least one edge extending arcuately intermediate said pair of end portions such that said at least one edge forms an arcuate sharp cutting edge;

one of said end portions being integrally formed with said juncture portion and the other of said end portions being fixed adjacent said juncture portion by a mechanical fastener means; and wherein said cutter portion is formed of a single band of material having a thickness defined by a maximum thickness of said band of material forming said cutter portion with said defined thickness substantially equal to said substantially uniform thickness of said band of material forming said shank portion.

2. The curette blade as set forth in claim 1 wherein said cutter portion is a loop-form cutter.

3. The curette blade as set forth in claim 2 wherein said arcuate sharp cutting edge is formed essentially as a complete loop to provide said loop-form cutter.

4. The curette blade as set forth in claim 3 wherein said loop form cutter is of a generally circular form.

5. The curette blade as set forth in claim 3 wherein said loop form cutter is of a generally elliptical form.

6. The curette blade as set forth in claim 3 wherein said loop form cutter is of a generally conical form.

7. The curette blade as set forth in claim 2 wherein said arcuate sharp cutting edge extends over approximately a 360 degree extent of said loop form cutter.

8. The curette blade as set forth in claim 3 wherein said shank portion is of a generally flat, thin section configuration extending on a plane and said loop-form cutter is generally symmetrical about said plane.

9. The curette blade as set forth in claim 8 wherein said arcuate sharp cutting edge extends over approximately a 180 degree extent of said loop-form cutter on either side of said plane.

10. The curette blade as set forth in claim 1 wherein said means for cooperation with a handle includes means for cooperation with a scalpel blade handle.

11. A disposable, single use curette blade comprising:

an elongated, unitary body member having an integrally formed shank portion, juncture portion and cutter portion with said juncture portion being disposed intermediate said shank portion and said cutter portion to connect said shank portion to said cutter portion;

said shank portion extending longitudinally from said juncture portion in one longitudinal direction and formed of a single band of material of a substantially uniform thickness, wherein only said shank portion of said curette blade extends in said one longitudinal direction beyond said juncture portion, said shank portion including means for cooperation with a handle to selectively, releasably retain said curette blade with respect to such a handle;

said cutter portion having at least one edge which forms a sharp cutting edge;

said cutter portion comprising a portion of said body member extending from said juncture portion as a generally arcuate means having a pair of end portions disposed adjacent said juncture portion and said at least one edge extending arcuately intermediate said pair of end portions such that said at least one edge forms an arcuate sharp cutting edge; and one of said end portions being integrally formed with said juncture portion and the other of said end portions being a free end residing adjacent but unattached to said juncture portion.

12. A disposable curette blade:

an elongated body member having a shank portion, a juncture portion and a cutter portion with said juncture portion being disposed intermediate said shank portion and said cutter portion to connect said shank portion to said cutter portion;

said shank portion extending longitudinally from said juncture portion in one longitudinal direction and in the shape of a single band of material of a substantially uniform thickness, wherein only said shank portion of said curette blade extends in said one longitudinal direction beyond said juncture portion, said shank portion including means for cooperation with the handle to retain said curette blade with respect to such a handle;

said cutter portion having at least one edge which forms a sharp cutting edge;

said cutter portion comprising a portion of said body member extending from said juncture portion and a generally arcuate means having a pair of end portions disposed adjacent said juncture portion and at least one edge extending arcuately intermediate said pair of end portions such that said at least one edge forms an arcuate sharp cutting edge;

one of said end portions being fixed adjacent said juncture portion by a mechanical fastener means; and wherein said cutter portion is formed of a single band of material having a thickness defined by a maximum thickness of said band of material forming said cutter portion with said defined thickness substantially equal to said substantially uniform thickness of said band of material forming said shank portion.

* * * * *

UNITED STATES PATENT AND TRADEMARK OFFICE
CERTIFICATE OF CORRECTION

PATENT NO.    : 6,001,113
DATED         : December 14, 1999
INVENTOR(S)   : Orin M. Goldblum It is certified that error appears in the above-identified patent and that said Letters Patent is hereby corrected as shown below:

Column 4 Line 20 "lok-Collet" should read --Lok-Collet--.

Column 7 Line 7 "in this alt" should read --in this art--.

Column 7 Line 64, Claim 3, "cutting edge" should read
    --cutting edge portion--.

Column 7 Line 67, Claim 4, "loop form cutter" should read
    --loop-form cutter--.

Column 8 Line 2, Claim 5, "loop form cutter" should read
    --loop-form cutter--.

Column 8 Line 4, Claim 6, "loop form cutter" should read
    --loop-form cutter--.

Column 8 Line 9, Claim 8, "in claim 3" should read
    --in claim 2--.

Signed and Sealed this

Twelfth Day of September, 2000

Attest:

Attesting Officer

Q. TODD DICKINSON

Director of Patents and Trademarks